United States Patent [19]

Reynolds, Jr. et al.

[11] 4,224,453
[45] Sep. 23, 1980

[54] ACYLATION OF A LACTONE-SUBSTITUTED ANILINE COMPOUND IN THE ABSENCE OF AN ACID ACCEPTOR

[75] Inventors: Richard N. Reynolds, Jr., Albany; Stephen D. Ziman, San Francisco; David C. K. Chan, Petaluma, all of Calif.

[73] Assignee: Chevron Research Company, San Francisco, Calif.

[21] Appl. No.: 18,489

[22] Filed: Mar. 8, 1979

Related U.S. Application Data

[63] Continuation of Ser. No. 847,504, Nov. 1, 1977, abandoned.

[51] Int. Cl.² .................. C07D 333/24; C07D 307/68; C07D 307/12
[52] U.S. Cl. .................................... 549/63; 260/347.3; 260/347.5
[58] Field of Search ..................... 260/332.2 R, 347.3, 260/347.5; 549/63

[56] References Cited

U.S. PATENT DOCUMENTS 3,933,860  1/1976  Chan ................................ 260/343.5

*Primary Examiner*—Alan Siegel
*Attorney, Agent, or Firm*—D. A. Newell; T. G. DeJonghe

[57] ABSTRACT

A process for making a compound of the formula

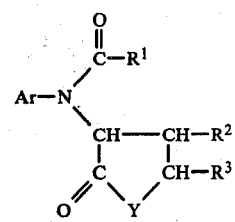

which process comprises contacting, in the absence of an acid acceptor, an acyl halide with an aniline substituted gamma-butyrolactone in the presence of a non-basic solvent and at a temperature between 65° and 150° C. Thus, 3-(N-chloroacetyl-N-2,6-dimethylphenylamino)-gamma-butyrolactone is prepared by a process comprising contacting, in the absence of an added acid acceptor, chloroacetylchloride with 3-(N-2,6-dimethylphenylamino)-gamma-butyrolactone in the presence of a non-basic organic solvent and at a temperature between 65° and 150° C. Preferably, the 3-(N-2,6-dimethylphenylamino)-gamma-butyrolactone is formed by reacting alpha-bromo-gamma-butyrolactone with dimethylaniline in the presence of water and in a non-basic organic solvent, and the 3-(N-2,6-dimethylphenylamino)-gamma-butyrolactone in the organic solvent is phase separated and fed straight through to the acetylation step.

12 Claims, No Drawings

ACYLATION OF A LACTONE-SUBSTITUTED ANILINE COMPOUND IN THE ABSENCE OF AN ACID ACCEPTOR

This is a continuation of application Ser. No. 847,504, filed Nov. 1, 1977, now abandoned.

BACKGROUND OF THE INVENTION

The present invention relates to the preparation of a haloacylated aniline compound. The compounds prepared in accordance with the process of the present invention are especially useful as fungicides.

The preparation of haloacylated aniline compounds is described in various references. For example, U.S. Pat. No. 3,268,584 relates to the preparation of various alpha-haloanilines. The Olin U.S. Pat. No. 3,268,584 states at column 3, lines 31 to 60:

"The alpha-haloacetanilides of this invention may in general be prepared by haloacetylation of suitable N-substituted and ortho-substituted aromatic amines, which may be prepared for example, by the process disclosed in application Ser. No. 824,455, filed July 2, 1959, now abandoned, from a primary aromatic amine and a branch-chain olefin. The haloacetylating agent is preferably either a haloacetic anhydride, such as chloroacetic anhydride, or a haloacetyl halide, such as chloroacetyl chloride, bromoacetyl bromide, or the like."

"The haloacetylation reaction is preferably conducted in the presence of a suitable liquid reaction medium. The liquid reaction medium must be anhydrous if the acetylating agent is a haloacetic anhydride; however, either anhydrous reaction mediums or mediums containing water can be used with haloacetyl halide acetylating agents. Examples of some suitable reaction mediums for use with either acetylating agent include benzene, diethyl ether, hexane, methylethyl ketone, chlorobenzene, toluene, chloroform, and the xylenes. Since an acid or hydrogen halide is eliminated in the haloacetylation reaction, it is also desirable to have an acid acceptor present in the reaction zone to neutralize the acid formed. Suitable acid acceptors for anhydrous solvent systems include the N-substituted ortho-substituted aromatic amine reactants, which may be present in the reaction zone in an amount greater than that required for the acetylation, tertiary amines, and pyridine. Acid acceptors in aqueous solvent systems include alkali or alkaline earth hydroxides and alkali or alkaline earth metal carbonates or bicarbonates."

As will be noted from the above, the Olin U.S. Pat. No. 3,268,584 teaches that it is desirable to have an acid acceptor present in the reaction zone wherein the haloacylation is conducted.

U.S. Pat. No. 3,345,151 also relates to the preparation of alpha-haloacetanilides and also teaches that the acylation reaction should be carried out in the presence of an acid acceptor.

U.S. Pat. No. 4,008,066 discloses the preparation of compounds of the formula

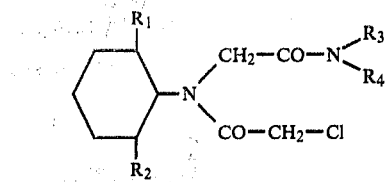

This U.S. Pat. No. 4,008,066 also teaches that the acylation reaction used to form the above compound advantageously is carried out in the presence of an acid acceptor, especially if chloroacetyl halides are used. The '066 patent states that it is possible to use an excess of the aniline compound which is being acylated as the acid acceptor. In Example 1 of the '066 patent, 2,6-dimethylaniline acetic acid methyl amide is acylated to form N-methyl-[N'-2,6-dimethylphenyl)-N'-chloroacetylamino]-acetamide by the reaction of the dimethylaniline with chloroacetyl chloride at a temperature of 110° C. From the amount of reactants used in the example, it is seen that a yield of about 50 mol percent is obtained with evidently 50% of the aniline compound fed to the acylation reaction being tied up as an acid acceptor.

U.S. Pat. No. 4,025,648 and German patent application No. 2,350,944 both relate to dimethylanilines having substituted on the aniline nitrogen a propionic acid methyl group and an alpha-halo acyl group. The disclosures of these references are similar but in the German reference the acyl group is acetyl whereas in U.S. Pat. No. 4,025,648 the acyl group is propionyl or higher. According to column 3 of the '648 patent, and similary in the last paragraph of page 13 of the German reference, preferably the acylation reaction used to form the acyl-substituted aniline compound is carried out in the presence of an acid acceptor such as trialkylamine, pyridine or an inorganic base such as a hydroxide or carbonate of an alkali metal. The '648 patent indicates that it is especially desirable to use an acid acceptor when the acylation is carried out using a haloacyl halide.

The use of an acid acceptor is not as critical when an acid anhydride is used for the acylation reaction because the resulting acid such as chloroacetic acid is much weaker than hydrogen chloride which results from the use of a chloroacyl for the acylation reaction. Thus, U.S. Pat. No. 3,875,228, Example 1, paragraph B shows a yield of about 72% for an acylation reaction carried out at about 100° C. when 4-isopropylamino indane is acylated with chloroacetic acid anhydride in the absence of an added acid acceptor.

The term "added acid acceptor" is used herein to mean a species which is added or fed to the reaction zone other than the feed aniline compound as, for example, an added tertiary amine which is capable of tying up hydrogen chloride acid released from the acylation reaction.

U.S. Pat. No. 3,933,860 to Chan discloses the preparation of haloacylated aniline compounds in the following reaction sequence:

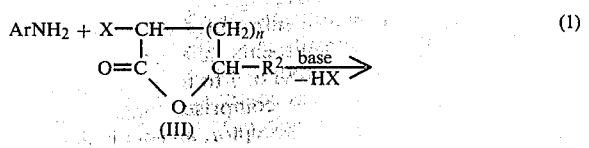

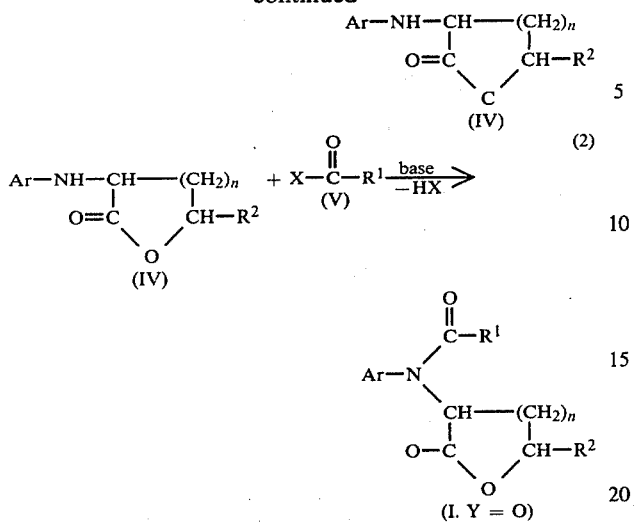

According to the Chan U.S. Pat. No. 3,933,860, the product (IV) of alkylation reaction (1):

"is generally purified by conventional procedures, e.g., extraction, distillation or crystallization, before use in the acylation reaction (2)."

"The acylation reaction (2) is conducted by conventional procedures in the presence of an organic amine such as a trialkyl amine or a pyridine compound. The reactants (IV) and (V) and the amine are generally contacted in substantially equimolar amounts in an inert organic solvent at a temperature of 0° to 100° C. Suitable inert organic solvents include ethyl acetate, methylene dichloride, dimethoxyethane, benzene, etc."

SUMMARY OF THE INVENTION

According to the present invention a process is provided for making a compound of the formula

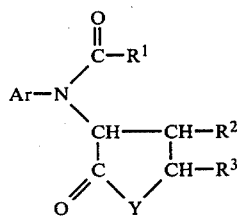

wherein Ar is phenyl or phenyl substituted with the same or different substituents selected from 1 to 5 alkyl and/or alkoxy groups of 1 to 4 carbon atoms; 1 or 2 fluoro, chloro and/or bromo; and 1 nitro; $R^1$ is alkyl, alkoxyalkyl or hydroxyalkyl of 1 to 4 carbon atoms unsubstituted or substituted with 1 to 4 fluoro, chloro or bromo; or phenyl or benzyl unsubstituted or substituted with the same or different substituents selected from 1 to 4 alkyl groups of 1 to 4 carbon atoms; 1 to 4 alkoxy groups of 1 to 4 carbon atoms; 1 to 4 fluoro, chloro and bromo; and 1 nitro group; $R^2$ is hydrogen or alkyl of 1 to 4 carbon atoms; $R^3$ is hydrogen, alkyl of 1 to 4 carbon atoms, phenyl or phenyl substituted with 1 to 2 of the same or different substituents selected from fluoro, chloro, bromo and/or alkyl of 1 to 6 carbon atoms; and Y is O or S, which process comprises contacting, in the absence of an added acid acceptor, an acyl halide of the formula $R^1C{=}OX$, wherein X is fluoro, chloro or bromo and $R^1$ is as previously defined, with a compound of the formula

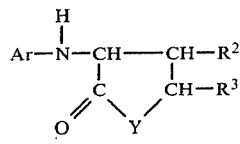

wherein Y, $R^2$ and $R^3$ are as previously defined, and wherein the contacting is carried out in the presence of a non-basic organic solvent and at a temperature between 65° and 150° C. to thereby obtain a formula I compound.

Preferably Ar is phenyl substituted with 1 to 2 alkyl groups of 1 to 4 carbon atoms; $R^1$ is alkyl of 1 to 4 carbon atoms unsubstituted or substituted with 1 to 4 chloro atoms; $R^2$ and $R^3$ are hydrogen or methyl, and Y is O. The terminology "hydrogen or methyl" means $R^2$ and $R^3$ may be the same or different. Preferably $R^2$ and $R^3$ are both hydrogen.

Particularly preferred Ar groups are those wherein Ar is phenyl substituted with an alkyl group of 1 to 3 carbon atoms in the 2-position and an alkyl group of 1 to 3 carbon atoms in the 6-position. Particularly preferred $R^1$ groups are alkyl groups of 1 to 4 carbon atoms unsubstituted or substituted with a chloro atom in the alpha position. Preferably X is chloro.

The process of the present invention can also be used to prepare compounds of the type mentioned in the commonly assigned application of co-inventor D. C. K. Chan entitled "Fungicidal 3-(N-acyl-N-arylamino)-gamma-butyrolactones and gamma-butyrothiolactones" filed on even data herewith, especially wherein the Ar group is naphthyl or substituted naphthyl as described in that application.

Preferred solvents for the present invention include benzene, chlorobenzene, xylene (meta, para and/or ortho), 1,2-dimethoxyethane, chloroform, and tetrahydrofuran. A particularly preferred solvent is toluene. The solvent preferably is a non-basic organic solvent which is substantially inert under the reaction conditions used.

Temperatures for the acylation reaction of the present invention are from 50° to 200° C., preferably 65° to 150° C., and more preferably from about 75° to 130° C. The preferred temperature is related to the solvent used. Thus, for benzene solvent, about 70°-90° C. is preferred and for use of a xylene solvent about 120°-140° C. is preferred.

Preferred pressures for the acylation reaction are about atmospheric or below, 1 psia to 20 psia. Pressures below atmospheric are preferred for solvents boiling below about 140° C.

According to a preferred embodiment of the present invention, a process is provided for making 3-(N-chloroacetyl-N-2,6-dimethylphenylamino)-gamma-butyrolactone which comprises (a) contacting, in the absence of an added acid acceptor, chloroacetyl chloride with 3-(N-2,6-dimethylphenylamino)-gamma-butyrolactone in the presence of a non-basic organic solvent and at a temperature between 65° and 150° C. to thereby obtain 3-(N-chloroacetyl-N-2,6-dimethylphenylamino)-gamma-butyrolactone in the organic solvent; and (b) separating the 3-(N-chloroacetyl-N-

2,6dimethylphenylamino)-gamma-butyrolactone from the organic solvent.

According to a preferred embodiment of the present invention wherein an "alkylation" reaction is included, a process is provided for making 3-(N-chloroacetyl-N-2,6-dimethylphenylamino)-gamma-butyrolactone which comprises (a) reacting alpha-bromolactone with 2,6-dimethyl aniline in the presence of water and a non-basic organic solvent at a temperature between 80° and 160° C. to form 3-(N-2,6-dimethylphenylamino)-gamma-butyrolactone in an organic phase of a two-phase aqueous-organic mixture; (b) separating the organic phase from the two-phase mixture; (c) contacting, in the absence of an added acid acceptor, the organic phase with chloroacetyl chloride at a temperature between 65° to 150° C., to thereby obtain 3-(N-chloroacetyl-N-2,6-dimethylphenylamino)-gamma-butyrolactone in the non-basic organic solvent; and (d) separating 3-(N-chloroacetyl-N-2,6-dimethylphenylamino)-gamma-butyrolactone from the organic solvent. The term "alkylation" is used herein to refer to that reaction step wherein a lactone is substituted onto the nitrogen of an aniline-type reactant.

Among other factors, the present invention is based on our finding that the acylation reaction in accordance with the present invention, especially wherein 3-(N-2,6-dimethylphenylphenylamino)-gamma-butyrolactone is reacted with chloroacetyl chloride to yield 3-(N-chloroacetyl-N-2,6-dimethylphenylamino)-gamma-butyrolactone, gives unexpectedly high yields when carried out in the absence of an added acid acceptor. The reasons for use of an acid acceptor in an acylation reaction include those given above under Background of the Invention. Generally, poor yields have been obtained when no added acid acceptor is used. Thus, note the 50% yield in U.S. Pat. No. 4,008,066 wherein no acid acceptor was used but instead the aniline type reactant evidently was tied up as an acid acceptor. However, omission of the acid acceptor in the particular reaction of the present invention results in several advantages, including increased adaptability of the process to a continuous flow commercial-type process and ease of recovery of the products, such as the 3-(N-chloroacetyl-N-2,6-dimethylphenylamino)-gamma-butyrolactone product. Instead of forming a salt by the reaction of the acid acceptor with the acid formed in the acylation reaction and then removing the salt by water washing, in the present invention the acid formed is removed from the acylation reaction mixture by heating above 65° C., usually above 80° C. and still very good yields are obtained. This 80° C. or higher temperature can be contrasted to the temperature of 37° to 46° C. used in the acylation reaction of Example 3, second paragraph, of U.S. Pat. No. 3,933,860.

Also, we have surprisingly found that in the instance of the thiolactone reactant for the alkylation, essentially no yield at all is obtained when the alkylation is carried out in the presence of a traditional acid acceptor such as pyridine, but that when no added acid acceptor is used we achieve good alkylation yields.

Thus, according to an especially preferred embodiment of the present invention, the alkylation reaction in accordance herewith is applied to butyrothiolactones, i.e., species wherein Y is S in the above-mentioned nomenclature.

Among other factors the preferred embodiment of the present invention referred to above wherein alkylation is included is based on the further discovery that the alkylation reaction step, wherein alpha-bromo-gamma-butyrolactone is reacted with dimethylaniline, gives high yields when carried out in the presence of water rather than merely washing the product of the reaction with water. Carrying out the alkylation reaction in the presence of water, present at the outset of the reaction, is advantageous in that it contributes to making the over-all process more readily adapted to a continuous commercial type process. Instead of a separate water wash step, water is present during the course of the alkylation reaction. We have found that large amounts of the alpha-bromo-gamma-butyrolactone are not lost by hydrolysis and that a good alkylation yield is achieved.

Preferred alkylation conditions are given in more detail in the commonly assigned application of co-inventor Richard N. Reynolds, Jr., titled "Alkylation of Aniline with a Lactone in the Presence of Water," filed on Nov. 1, 1977, now U.S. Pat. No. 4,165,322.

A surprisingly advantageous embodiment of the present invention, especially in terms of economy of operation, is one wherein the above "straight-through" type processing is expanded to also include the production of the bromolactone species used in the alkylation step in the same solvent, e.g., toluene, that carries through to the alkylation and acylation steps. The production of the bromolactone is carried out by contacting bromine with the lactone in the presence of a phosphorus catalyst.

EXAMPLES

Example 1—Preparation of 3-(N-2,6-dimethylphenylamino)-gamma-butyrolactone

An aqueous/toluene mixture of alpha-bromo-gamma-butyrolactone and dimethylaniline in a molar ratio of one mol lactone to 2.1 mols of aniline compound was heated with stirring at 92° C. for 18 hours. This resulted in the reaction of the lactone with the aniline compound to obtain 3-(N-2,6-dimethylphenylamino)-gamma-butyrolactone in the organic phase. The aqueous phase contained excess dimethylaniline combined with hydrogen bromide to thus form a salt. The aqueous phase containing the dimethylaniline hydrogen bromide salt was phase separated from the organic phase.

The organic phase was washed with an aqueous solution containing 5% hydrochloric acid to remove residual dimethylaniline. Water was azeotropically distilled from the organic phase, i.e., toluene solution containing 3-(N-2,6-dimethylphenylamino)-gamma-butyrolactone. A portion of this solution remaining after removal of the water was stripped by vacuum suction to give a sample for toxicology analysis. The remaining portion was retained for acetylation of 3-(N-2,6-dimethylphenylamino)-gamma-butyrolactone in accordance with Example 2 below.

The composition of the toluene mixture before and after the reaction of the bromobutyrolactone with dimethylaniline is summarized in Table I below:

TABLE I

| Component | Before (wt. %) | After Reaction of Product (wt. %) |
|---|---|---|
| Bromobutyrolactone | 19.2 | 1.5 |
| Dimethylaniline | 29.7 | — |
| Toluene | 22.3 | 51.2 |
| Water | 25.7 | — |
| Bromobutyrolactone impurities | 3.2 | — |
| 3-(N-2,6-dimethylphenyl | | |

TABLE I-continued

| Component | Before (wt. %) | After Reaction of Product (wt. %) |
|---|---|---|
| amino)-gamma-butyrolactone | | 40.8 |
| 3-(N-2,6-dimethylphenyl amino)-gamma-butyrolactone | | |
| impurities | | 6.5 |

EXAMPLE 2—Preparation of 3-(N-chloroacetyl-N-2,6dimethylphenylamino)-gamma-butyrolactone The toluene solution of 3-(N-2,6-dimethylphenylamino)-gamma-butyrolactone, which contained about 40.8 weight percent 3-(N-2,6-dimethylphenylamino-gamma-butyrolactone, was chloroacetylated with 1.3 molar equivalents of chloroacetyl chloride to obtain 3-(N-chloroacetyl-N-2,6-dimethylphenylamino)-gamma-butyrolactone. This reaction was carried out by contacting the toluene solution of 3-(N-2,6-dimethylphenylamino)-gamma-butyrolactone with the chloroacetyl chloride at a temperature of about 105°-118° C. with stirring and with 15 minutes of heating at 110° C. after the chloroacetyl chloride had been added to the toluene solution.

After the heating at 110° C., the solution was cooled to 20° C. and the resultant thick slurry was filtered. The crude cake was reslurried twice with fresh toluene, 33 weight percent toluene by weight of 3-(N-chloroacetyl-N-2,6-dimethylphenylamino)-gamma-butyrolactone in the slurry each time, and then air dried.

The over-all yield of 3-(N-chloroacetyl-N-2,6-dimethylphenylamino)-gamma-butyrolactone from bromo-butyrolactone was about 66%.

EXAMPLE 3

A mixture of 1.05 mols of 2,6-dimethylaniline, 0.48 mols of alpha-bromo-gamma-butyrothiolactone, 65 ml of toluene and 65 ml of water was refluxed for 18 hours at about 85° C. This resulted in the reaction of the lactone compound with the aniline compound to obtain an alkylation product in the organic phase, namely 3-(N-2,6-dimethylphenylamino)-gamma-butyrothiolactone. The mixture obtained after refluxing was poured into 500 ml of dichloromethane and washed with 100 ml water and 200 ml 5% HCl aqueous solution. After phase separating the organic phase containing the alkylation product, the organic phase was given a second wash with 200 ml of water. The organic phase was again phase separated and then was dried using magnesium sulfate. After the magnesium sulfate drying step, the organic solvent was removed by evaporation at about 75° C. About 98 g of a brown viscous material was obtained. NMR (nuclear magnetic resonance) analysis of the crude product indicated the crude material was primarily the desired alkylate product.

The crude product was mixed with 500 ml toluene and a solid by-product material was removed from the crude product. The toluene was then removed by evaporation to obtain a yield of about 90 g (85% yield) of the alkylate product.

The alkylate product was added to 1000 ml toluene and heated to reflux. The chloroacetyl chloride was added dropwise over about 1 hour's time. The amount of the chloroacetyl chloride reactant was 0.4 mols and similarly the amount of the alkylate reactant was 0.4 mol. The refluxing was continued until hydrogen chloride gas ceased to be evolved. After workup, a yield of about 65 g of acylated product, namely 3-(N-chloroacetyl-N-2,6-dimethylphenylamino)-gamma-butyrothiolactone, was obtained.

EXAMPLE 4—Preparation of 3-(N-chloroacetyl-N-2,6-dimethylphenyl)-gamma-butyrothiolactone A solution of 10 g (0.055 mol) alpha-bromo-gamma-butyrothiolactone, 6.68 g (0.055 mol) 2,6-dimethylaniline and 5.58 g (0.055 mol) dimethylpyridine was heated at 85°-90° C. for 12 hours. The reaction mixture was then cooled, diluted with water and dichloromethane. The organic phase was separated and filtered through a short silica gel column. The filtrate was evaporated under reduced pressure to give an oil residue. The residue was washed with 5% aqueous hydrochloric acid solution, washed with water, and dried over magnesium sulfate to give 7.2 g of 3-(N-dimethylphenylamino)-gamma-butyrothiolactone. The infrared spectrum of the thiolactone product showed strong carbonyl absorption at 5.88 micron.

Elemental analysis for $C_{12}H_{15}NOS$ showed: %S, calc. 14.5, found 14.2.

A solution of 1.52 g (0.0134 mol) chloroacetyl chloride in 10 ml toluene was added dropwise to a solution of 2.97 g (0.0134 mol) 3-(N-dimethylphenylamino)-gamma-butyrothiolactone in 100 ml benzene maintained at reflux temperature. The reaction mixture was heated at reflux until the evolution of hydrochloride gas ceased (about 3 hours), cooled, and evaporated under reduced pressure to give a brown solid. Recrystallization form isopropanol gave 2.5 g of 3-(N-chloroacetyl-N-2,6-dimethylphenylamino)-gamma-butyrothiolactone, as tan crystals, m.p. 138°-139° C. The infrared spectrum of the product showed two strong carbonyl absorption bands at 5.88 microns and 6.02 microns. Elemental analys for $C_{14}H_{16}ClNO_2S$ showed: %S, calc. 10.8, found 10.8; %Cl, calc. 12.0, found 13.6.

EXAMPLE 5—Preparation of 3-(N-chloroacetyl-N-2-chloro-6-methylphenylamino)-gamma-butyrothiolactone A solution of 8 g (0.044 mol) alpha-bromo-gamma-butyrothiolactone, 6.23 g (0.044 mol) 2-chloro-6-methylaniline and 4.7 g (0.044 mol) 2,6-dimethylpyridine was heated for about 16 hours at about 95° C. under a nitrogen atmosphere. The reaction mixture was cooled, diluted with 60 ml dichloromethane, washed with water, washed with 10% aqueous hydrochloric acid, and filtered. The filtrate was dried over magnesium sulfate and evaporated under reduced pressure to give a dark viscous residue. The residue was eluted through a short silica gel chromatography column with dichloromethane. The product-containing fractions were stripped to give 4.59 g of 3-(N-2-chloro-6-methyl-phenylamino)-gamma-butyrothiolactone. Thin-layer chromatography of the product showed one large spot. The infrared spectrum of the product showed strong carbonyl absorption at 5.88 micron and the nuclear magnetic resonance spectrum showed a 3-proton singlet for the methyl group at 2.33 ppm (relative to tetramethylsilane).

A solution of 2.15 g (0.019 mol) chloroacetyl chloride in 10 ml toluene was added dropwise to a refluxing solution of 4.59 g (0.019 mol) 3-(N-2-chloro-6-methylphenylamino)-gamma-butyrothiolactone in 150 ml toluene. The reaction mixture was heated at reflux for about 7 hours (HCl was evolved), stirred about 16 hours at 25° C. and evaporated under reduced pressure to give a dark residue. Thin-layer chromatography of the residue showed two spots. The residue was chromatographed through a silica-gel column with acetone/dichloromethane elution. The chromatographic fractions containing the second material eluted from the column were combined and evaporated to give the desired product, which was crystallized from isopropyl alcohol to give 0.98 g of product, as a brown solid, m.p. 133°–137° C. The infrared spectrum of the product showed two strong carbonyl absorption bands at 5.84 microns and 5.95 microns. Elemental analysis for $C_{13}H_{13}Cl_2NO_2S$ showed: %S, calc. 10.0, found 11.0; %Cl, calc. 22.3, found 23.6.

EXAMPLE 6—Preparation of 3-(N-methoxymethyl-N-2,6-dimethylphenylamino)-gamma-butyrothiolactone A solution of 1.46 g (0.0135 mol) methoxyacetyl chloride in 10 ml toluene was added dropwise to a refluxing solution of 3 g (0.0135 mol) 3-(N-2,6-dimethylphenyamino)-gamma-butyrothiolactone in 200 ml toluene. The reaction mixture was heated at reflux for 3 hours and evaporated to give a solid. The solid was recrystallized from a 10:1:10 solvent mixture of ether:-benzene:hexane to give 1.8 g of the product, as a tan solid, m.p. 86°–87° C. The infrared spectrum of the product showed two strong carbonyl absorption bands at 5.85 microns and 6.03 microns. Elemental analysis for $C_{15}H_{19}NO_3S$ showed: %S, calc. 10.9, found 11.2.

EXAMPLES 7–20

Other compounds prepared in accordance with the present invention using no acid acceptor and with yields generally 60% or higher for the acylation reaction are summarized in Tables II and III below.

As may be noted from the above examples, preferably the amount of alkylate feed is about 1 mol per mol of acyl halide feed to the process of the present invention. More preferably a slight excess of acyl halide, for example about 1.01 to 1.1 mols acyl halide reactant such as the chloroacetyl chloride, is used per mol or alkylate feed. Thus the alkylate compound is not added in stoichiometric excess amounts to act as an added acid acceptor, such as would be the case in prior art reactions where aniline reactants may be used in approximately 2 mols per mol of acyl halide feed.

TABLE II

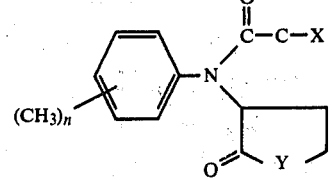

| Ex. No. | RE | n(position) | X | Y |
| --- | --- | --- | --- | --- |
| 7 | 27210 | 2(2,3) | Cl | S |
| 8 | 27212 | 2(2,3) | OCH₃ | S |
| 9 | 27484 | 3(2,3,6) | Cl | O |
| 10 | 27485 | 3(2,3,6) | OCH₃ | O |
| 11 | 27710 | 3(2,3,6) | Cl | S |
| 12 | 27709 | 3(2,3,6) | OCH₃ | S |
| 13 | 27783 | 4(2,3,5,6) | Cl | O |
| 14 | 27784 | 4(2,3,5,6) | OCH₃ | O |
| 15 | 27785 | 4(2,3,5,6) | Cl | S |

TABLE II-continued

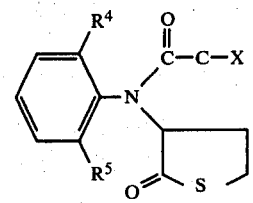

| Ex. No. | RE | n(position) | X | Y |
| --- | --- | --- | --- | --- |
| 16 | 27786 | 4(2,3,5,6) | OCH₃ | S |

TABLE III

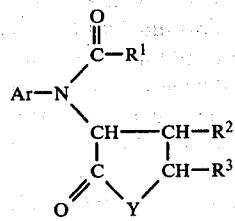

| Ex. No. | RE | R⁴ | R⁵ | X |
| --- | --- | --- | --- | --- |
| 17 | 27108 | C₂H₅ | C₂H₅ | Cl |
| 18 | 27109 | C₂H₅ | C₂H₅ | OCH₃ |
| 19 | 27565 | C₂H₅ | CH₃ | Cl |
| 20 | 27566 | C₂H₅ | CH₃ | OCH₃ |

What is claimed is:
1. A process for making a compound of the formula

wherein Ar is phenyl or phenyl substituted with the same or different substituents selected from 1 to 5 alkyl and/or alkoxy groups of 1 to 4 carbon atoms; 1 or 2 fluoro, chloro and/or bromo; and 1 nitro;

R¹ is alkyl, alkoxyalkyl or hydroxyalkyl of 1 to 4 carbon atoms unsubstituted or substituted with 1 to 4 fluoro, chloro or bromo; or phenyl or benzyl unsubstituted or substituted with the same or different substituents selected from 1 to 4 alkyl groups of 1 to 4 carbon atoms; 1 to 4 alkoxy groups of 1 to 4 carbon atoms; 1 to 4 fluoro, chloro and bromo; and 1 nitro group;

R² is hydrogen or alkyl of 1 to 4 carbon atoms;

R³ is hydrogen, alkyl of 1 to 4 carbon atoms, phenyl or phenyl substituted with 1 to 2 of the same or different substituents selected from fluoro, chloro, bromo and/or alkyl of 1 to 6 carbon atoms; and Y is O or S;

which comprises:
contacting, in the absence of an added acid acceptor, an acyl halide of the formula $$R^1\overset{O}{\overset{\|}{C}}X$$

wherein X is fluoro, chloro or bromo and $R^1$ is as previously defined, with a compound of the formula

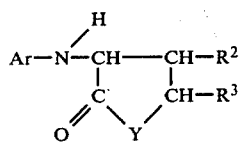

II wherein Y, $R^2$ and $R^3$ are as previously defined and wherein the contacting is carried out in the presence of a non-basic organic solvent at a temperature between 65° and 150° C., and without any stoichiometric excess of formula II compound based on the mols of the acyl halide reactant, to thereby obtain a formula 1 compound.

2. A process in accordance with claim 1 wherein Y is S.

3. A process in accordance with claim 1 wherein:
Ar is phenyl substituted with 1 to 2 alkyl groups of 1 to 4 carbon atoms;
$R^1$ is alkyl or alkoxyalkyl of 1 to 4 carbon atoms unsubstituted or substituted with 1 to 4 chloro atoms;
$R^3$ and $R^2$ are hydrogen or methyl, and
Y is O or S.

4. A process in accordance with claim 3 wherein Y is S.

5. A process in accordance with claim 3 wherein the solvent is toluene.

6. A process in accordance with claim 5 wherein
Ar is phenyl substituted with an alkyl group of 1 to 3 carbon atoms in the 2-position and an alkyl group of 1 to 3 carbon atoms in the 6-position, and $R^1$ is an alkyl group of 1 to 4 carbon atoms unsubstituted or substituted with a chloro atom in the alpha position and X is chloro.

7. A process for making 3-(N-chloroacetyl-N-2,6dimethylphenylamino)-gamma-butyrolactone which comprises:
(a) contacting, in the absence of an added acid acceptor, chloroacetyl chloride with 3-(N-2,6-dimethylphenylamino)-gamma-butyrolactone in the presence of a non-basic organic solvent at a temperature between 80° and 150° C., and without any stoichiometric excess of 3-(N-2,6-dimethylphenylamino)-gamma-butyrolactone compound based on the mols of the acyl halide reactant, to thereby obtain 3-(N-chloroacetyl-N-2,6-dimethylphenylamino)-gamma-butyrolactone in the organic solvent; and
(b) separating the 3-(N-chloroacetyl-N-2,6-dimethylphenylamino)-gamma-butyrolactone from the organic solvent.

8. A process in accordance with claim 7 wherein the organic solvent is toluene.

9. A process for making 3-(N-chloroacetone-N-2,6-dimethylphenylamino)-gamma-butyrothiolactone which comprises:
(a) contacting, in the absence of an added acid acceptor, chloroacetyl chloride with 3-(N-2,6-dimethylphenylamino)-gamma-butyrothiolactone in the presence of a non-basic organic solvent at a temperature between 80° and 150° C., and without any stoichiometric excess of 3-(N-2,6-dimethylphenylamino)-gamma-butyrolactone compound based on the mols of the acyl halide reactant, to thereby obtain 3-(N-chloroacetyl-N-2,6-dimethylphenylamino)-gamma-butyrothiolactone in the organic solvent; and
(b) separating the 3-(N-chloroacetyl-N-2,6-dimethylphenylamino)-gamma-butyrothiolactone from the organic solvent.

10. A process for making 3-(N-methoxyacetyl-N-2,6-dimethylphenylamino)-gamma-butyrothiolactone which comprises:
(a) contacting in the absence of an added acid acceptor, methoxyacetyl chloride with 3-(N-2,6-dimethylphenylamino)-gamma-butyrothiolactone in the presence of a non-basic organic solvent at a temperature between 80° and 150° C., and without any stoichiometric excess of 3-(N-2,6-dimethylphenylamino)-gamma-butyrolactone compound based on the mols of the acyl halide reactant, to thereby obtain 3-(N-methoxyacetyl-N-2,6-dimethylphenylamino)-gamma-butyrothiolactone in the organic solvent; and
(b) separating the 3-(N-methoxyacetyl-N-2,6-dimethylphenylamino)-gamma-butyrothiolactone from the organic solvent.

11. A process for making 3-(N-chloroacetyl-N-2,6dimethylphenylamino)-gamma-butyrolactone which comprises:
(a) reacting alpha-bromo-gamma-butyrolactone with 2,6-dimethyl aniline in the presence of water and a non-basic organic solvent at a temperature between 80° and 160° C. to form 3-(N-2,6dimethylphenylamino)-gamma-butyrolactone in an organic phase of a two-phase aqueous-organic mixture;
(b) separating the organic phase from the two-phase mixture;
(c) contacting, in the absence of an added acid acceptor, the organic phase with chloroacetylchloride at a temperature between 65° and 150° C., and without any stoichiometric excess of 3-(N-2,6-dimethylphenylamino)-gamma-butyrolactone compound based on the mols of acyl halide reactant, to thereby obtain 3-(N-chloroacetyl-N-2,6-dimethylphenylamino)gamma-butyrolactone in the nonbasic organic solvent; and
(d) separating 3-(N-chloroacetyl-N-2,6-dimethylphenylamino)-gamma-butyrolactone from the organic solvent.

12. A process in accordance with claim 11 wherein the organic solvent is toluene.

* * * * *